United States Patent
Ferruti et al.

(10) Patent No.: US 8,372,933 B2
(45) Date of Patent: Feb. 12, 2013

(54) HYPERBRANCHED POLYMERS BASED ON CYCLODEXTRINS AND POLY (AMIDOAMINES) FOR THE CONTROLLED RELEASE OF INSOLUBLE DRUGS

(75) Inventors: Paolo Ferruti, Milan (IT); Elisabetta Ranucci, Opera (IT); Francesco Trotta, Asti (IT); Roberta Cavalli, Alessandria (IT); Claudio Fernandez, Allo (ES)

(73) Assignee: L'Urederra Fundacion Para el Desarrollo Tecnologico y Social, Los Arcos (ES)

( * ) Notice: Subject to any disclaimer, the term of this patent is extended or adjusted under 35 U.S.C. 154(b) by 279 days.

(21) Appl. No.: 12/663,999

(22) PCT Filed: Jun. 10, 2008

(86) PCT No.: PCT/EP2008/004624
§ 371 (c)(1),
(2), (4) Date: Apr. 1, 2010

(87) PCT Pub. No.: WO2008/151775
PCT Pub. Date: Dec. 18, 2008

(65) Prior Publication Data
US 2010/0184712 A1    Jul. 22, 2010

(30) Foreign Application Priority Data
Jun. 11, 2007   (IT) .............................. MI2007A1173

(51) Int. Cl.
C08F 251/00 (2006.01)
C08G 73/02 (2006.01)
C08G 73/06 (2006.01)
A61K 31/724 (2006.01)

(52) U.S. Cl. ......... 527/312; 527/313; 527/314; 527/315; 424/487; 424/488; 514/58; 536/103; 536/124

(58) Field of Classification Search ................. None
See application file for complete search history.

(56) References Cited

U.S. PATENT DOCUMENTS 5,985,916 A    11/1999   Duncan et al.
2005/0043481 A1*  2/2005  Gref et al. ............... 525/54.2

OTHER PUBLICATIONS

Cao, Z. et al "Synthesis and characterization of a novel polyamidoamine dendrimer . . ." Gaofenzi Cailiao Kexue Yu Gongcheng (2007) vol. 23, No. 5 pp. 53-56 (Caplus abstract only).*
Wang, D. et al "Preparation and characterization of novel hyperbranched poly(amidoamines) . . ." J. Polym. Sci. Part A: Polym. Chem. (2005) vol. 43, pp. 5127-5137.*
Kang, J. et al "Cyclodextrin complexation: influence on the solubility . . . " Eur. J. Pharm. Sci. (2002) vol. 15, pp. 163-170.*

* cited by examiner

*Primary Examiner* — Leigh Maier
(74) *Attorney, Agent, or Firm* — Arent Fox LLP

(57) ABSTRACT

Hyperbranched, water-soluble polymers, obtainable by Michael polyaddition of α-, β-, or γ-cyclodextrins and amines to bisacrylamides.

5 Claims, 11 Drawing Sheets

Figure 1: General structure of the hyperbranched PAA/cyclodextrin polymers of the present invention
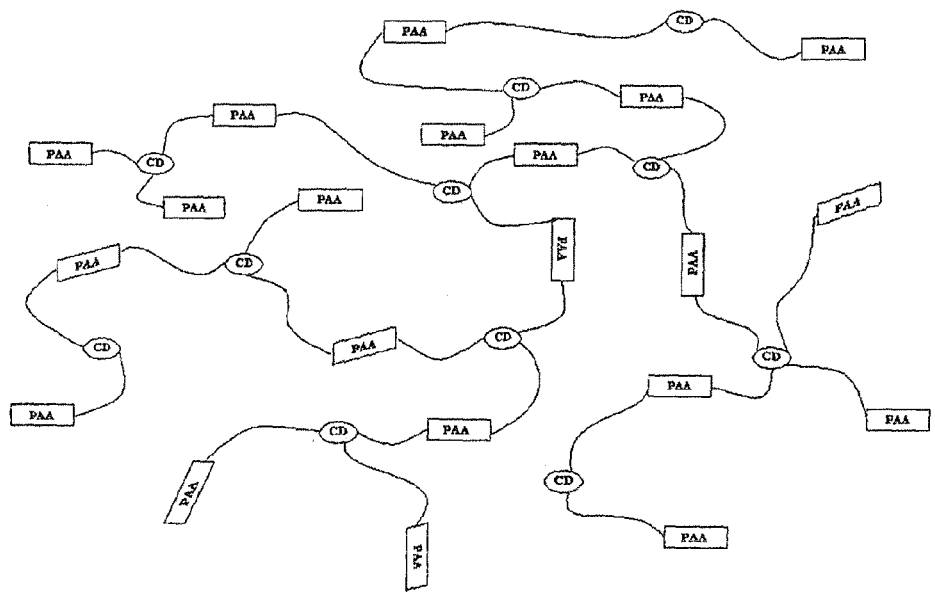
CD = Cyclodextrin units
PAA = Poly(amidoamine) segments Figure 2: Structure of the of the hyperbranched PAA/β-cyclodextrin polymer synthesized as reported in Example 1
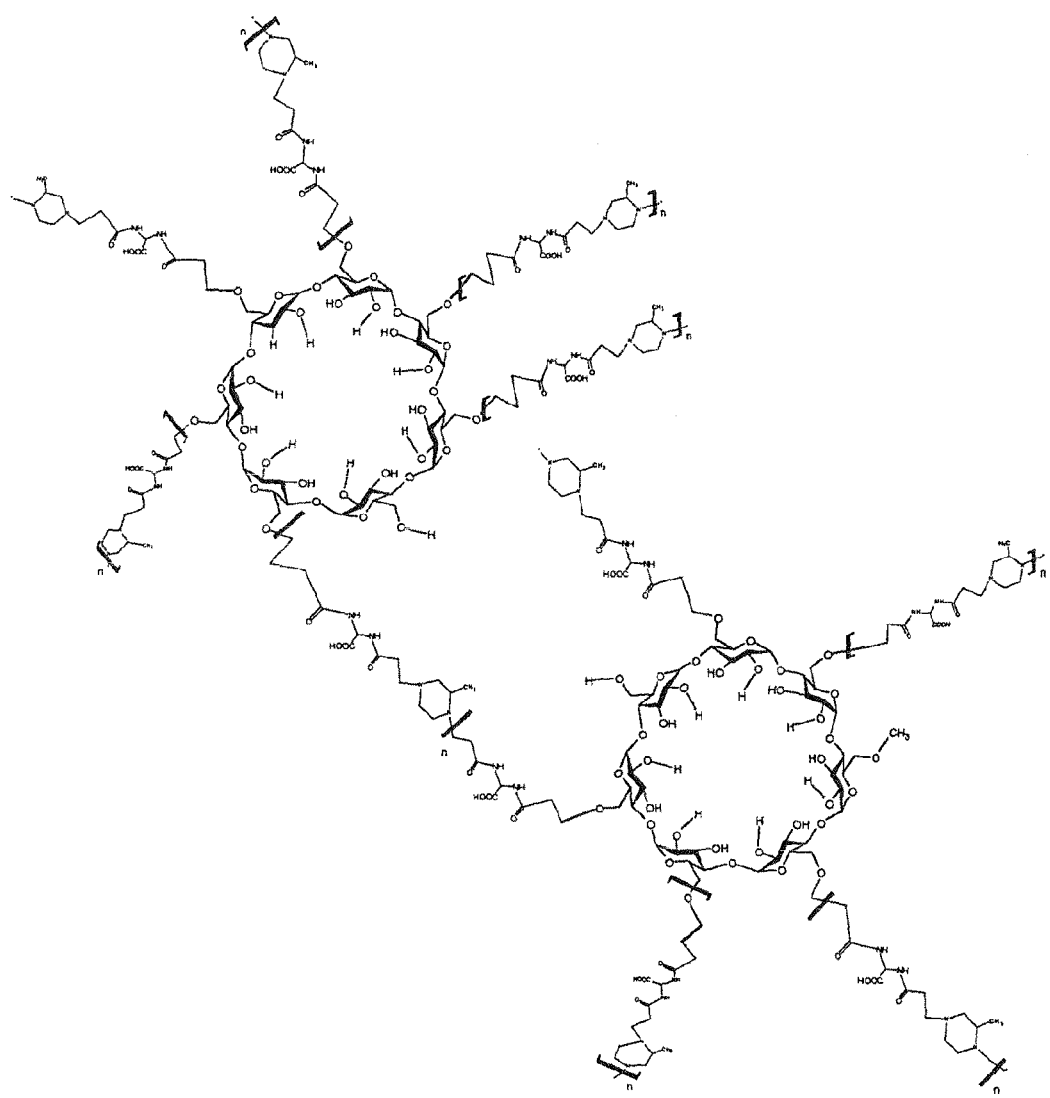

Figure 3: 1H NMR spectrum of the hyperbranched PAA/β-cyclodextrin polymer synthesized as reported in Example 1
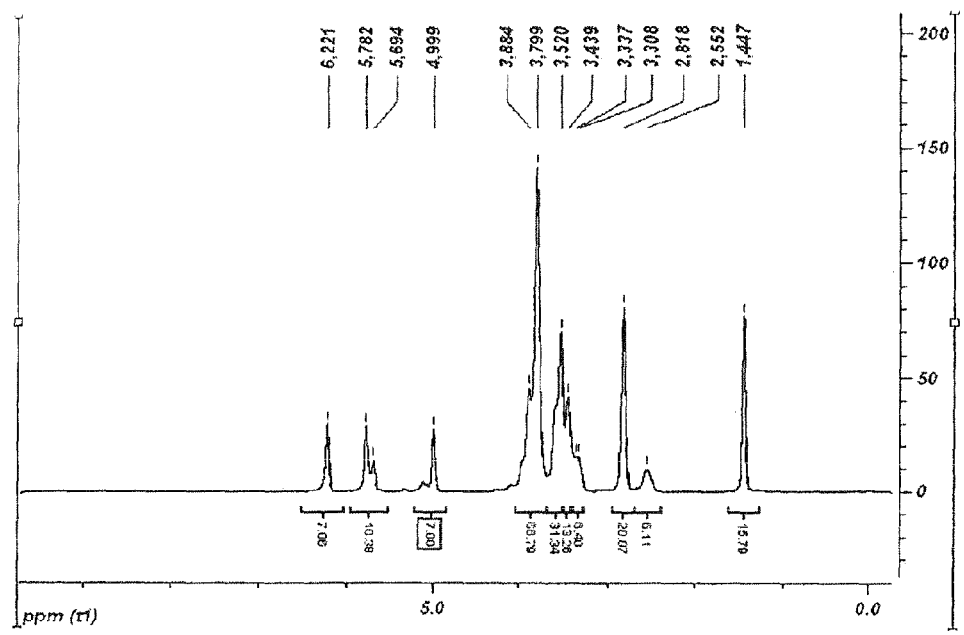

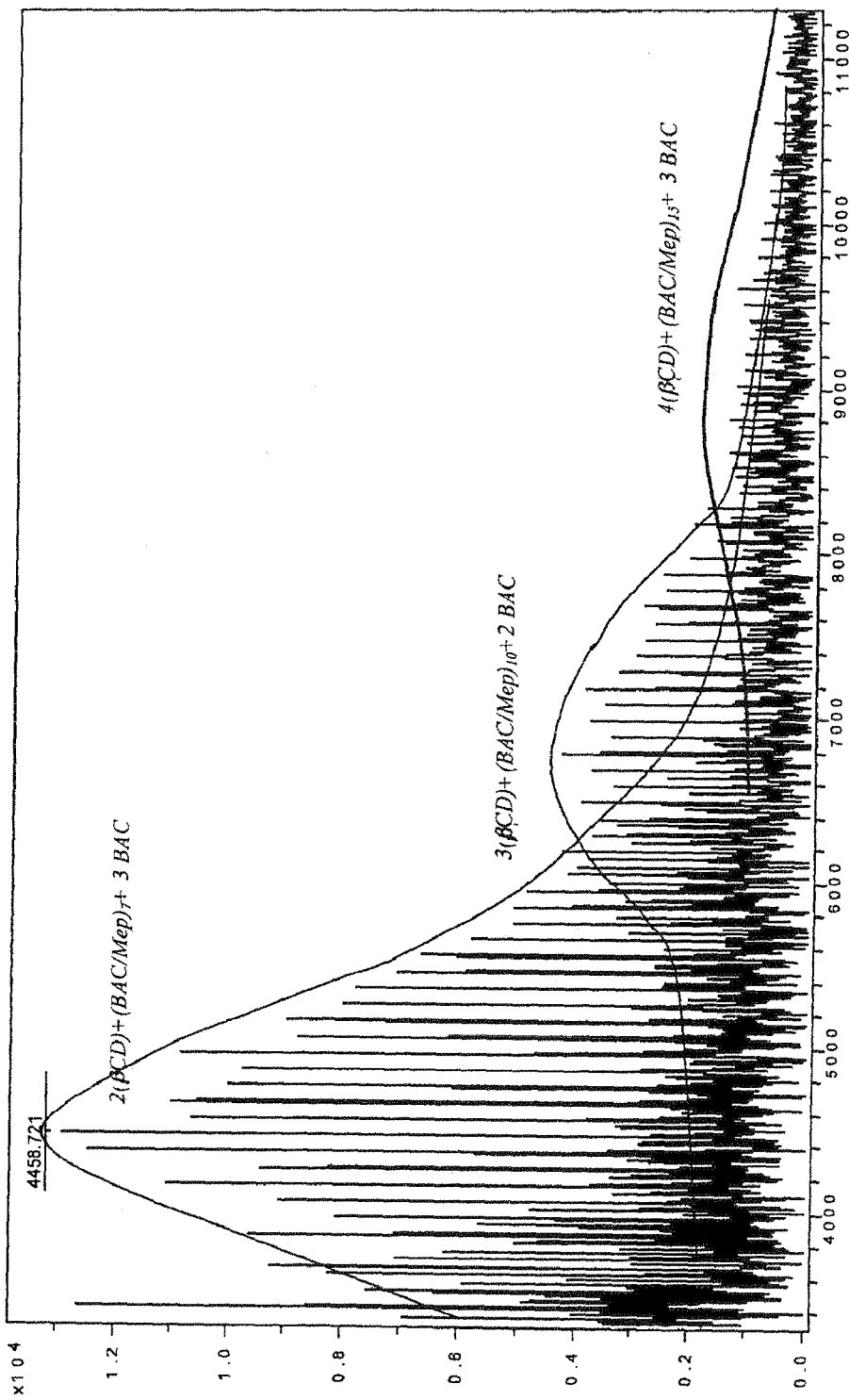
Figure 4: MALDI-TOF spectrum of the polymer of Example 1.

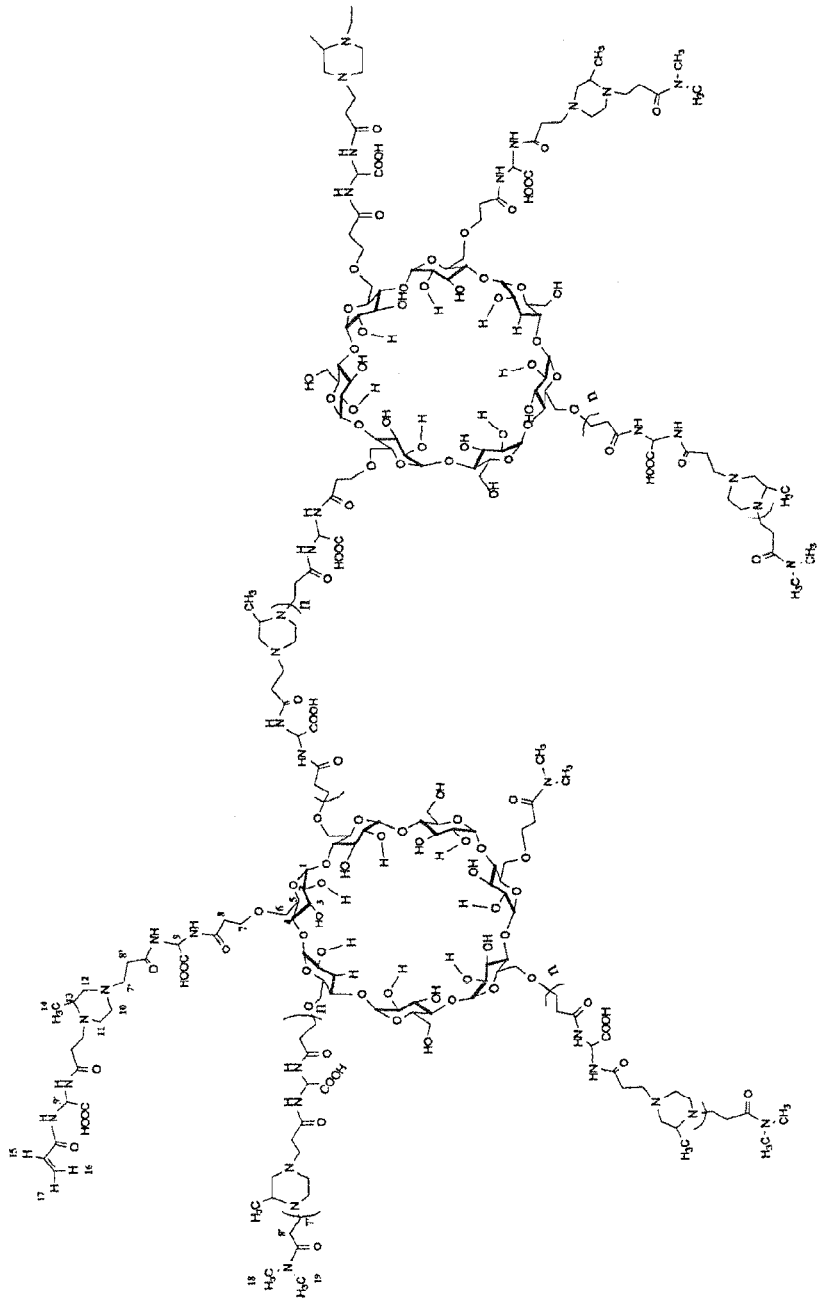
Figure 5: Schematic representation of the hyperbranched PAA/β-cyclodextrin synthesized with N,N'-dimethylacrylamide as monofunctional chain terminator (Example 2)

Figure 6: ¹H NMR spectrum of the hyper-branched PAA/β-cyclodextrin synthesized with N,N'-dimethylacrylamide as chain terminator (Example 2).
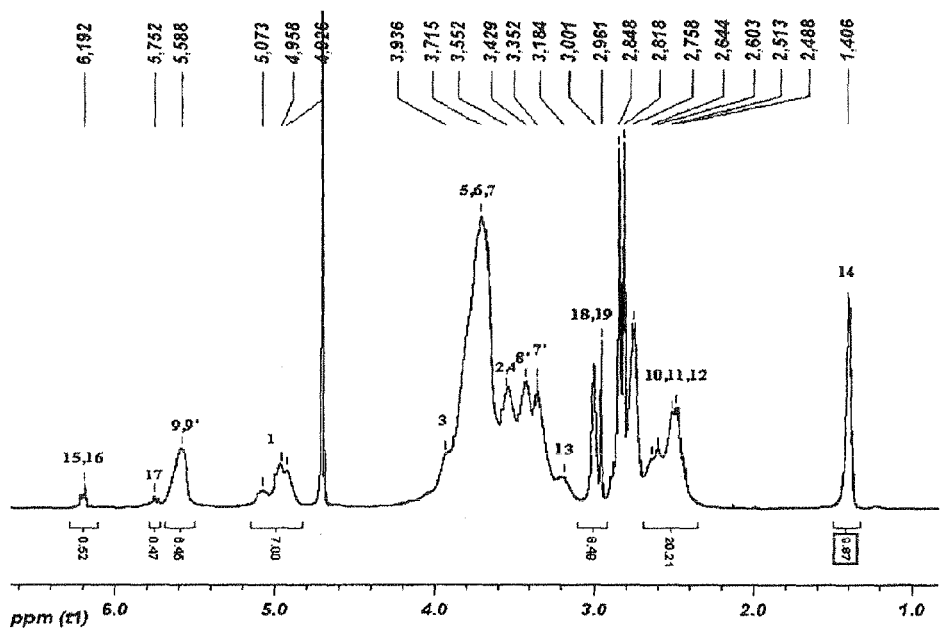

Figure 7: TEM micrograph of polymer of Example 3 from aqueous dispersions (magnification: 69000 x)
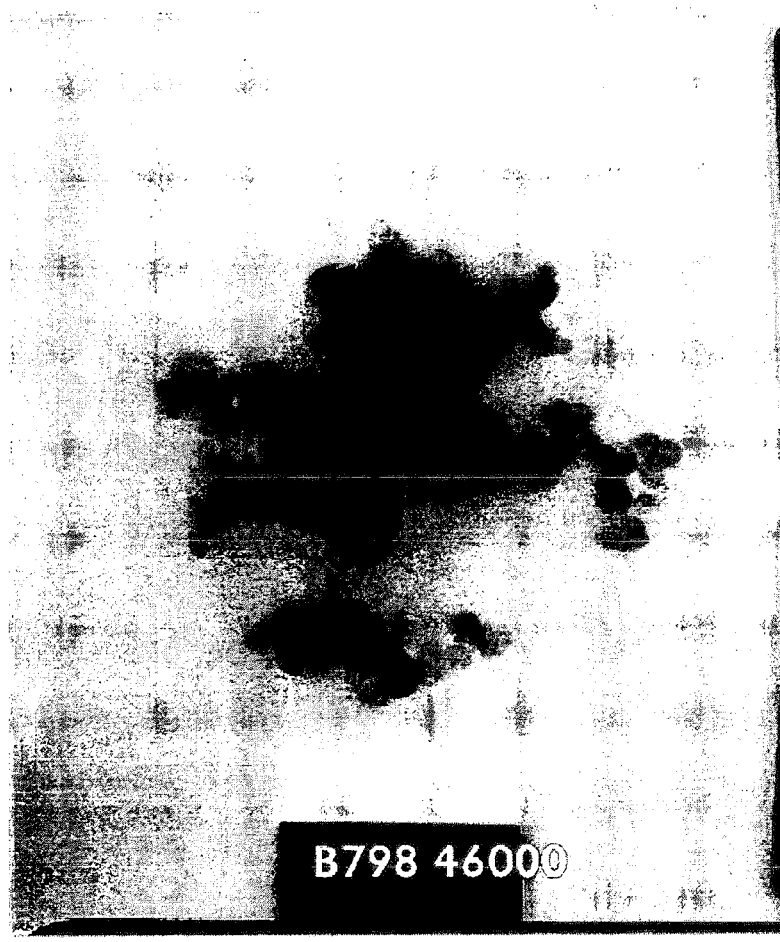

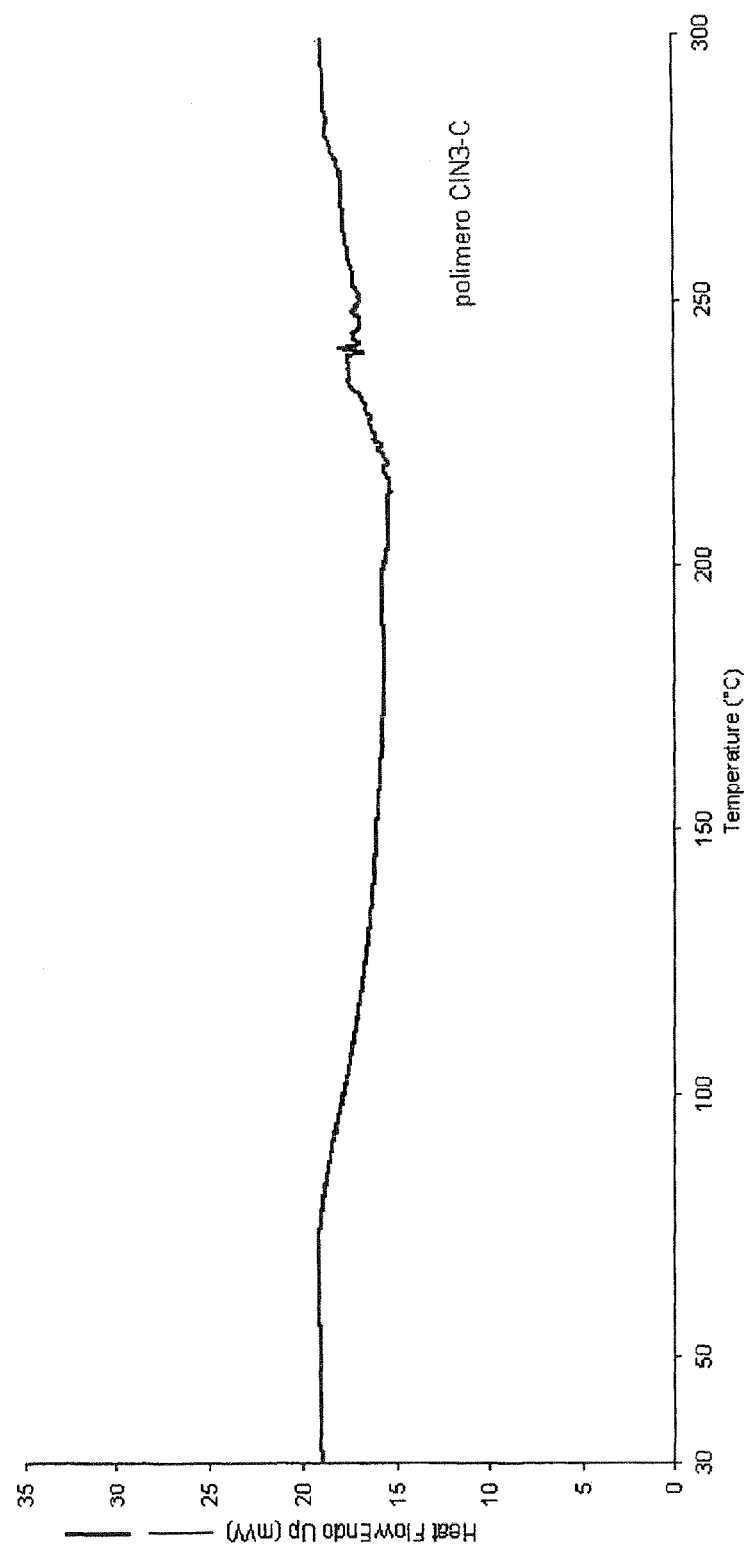
Figure 8: DSC tracing of the polymer reported in Example 3.

Figure 9: TEM micrographs of the Paclitaxel complex of the polymer reported in Example 3 before (a) and after (b) lyophilization of its aqueous dispersions.
(a)
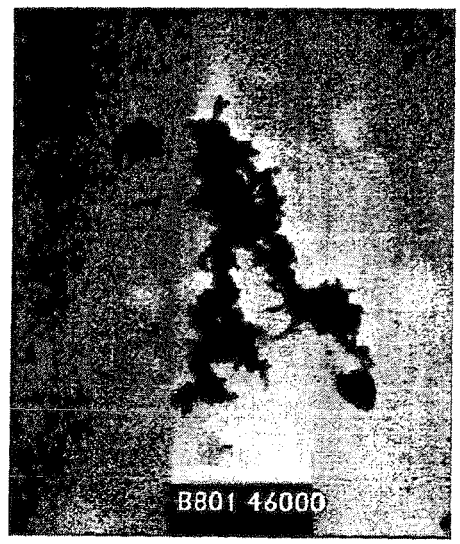
(b)

Figure 10: Paclitaxel release kinetics from it complexes with typical hyperbranched PAA-cyclodextrin polymers.
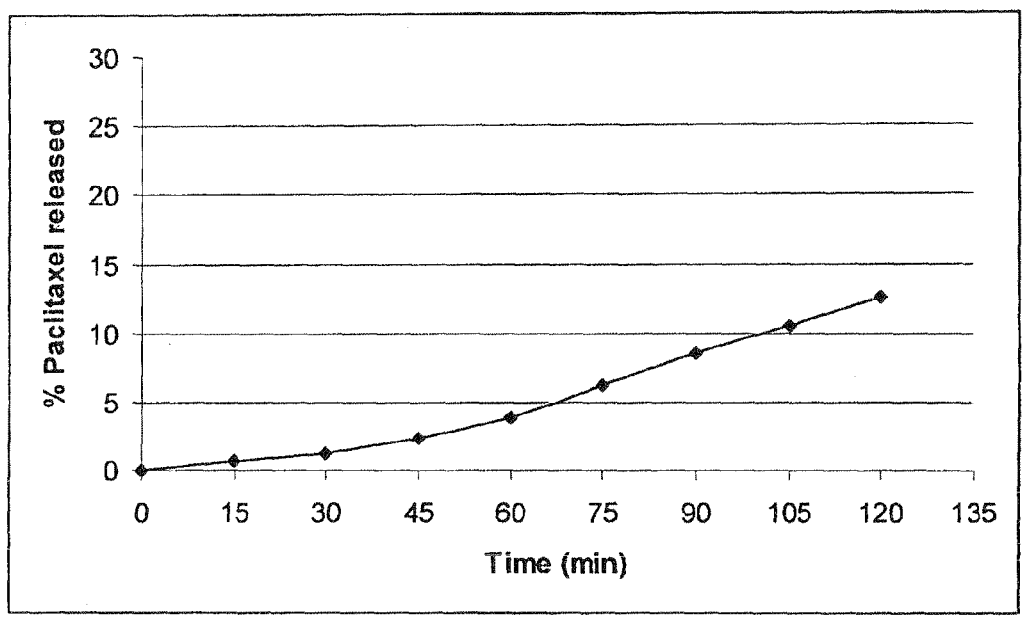

Figure 11: In vitro cytotoxicity assays of free paclitaxel and its complexes with hyperbranched PAA-cyclodextrin polymers.
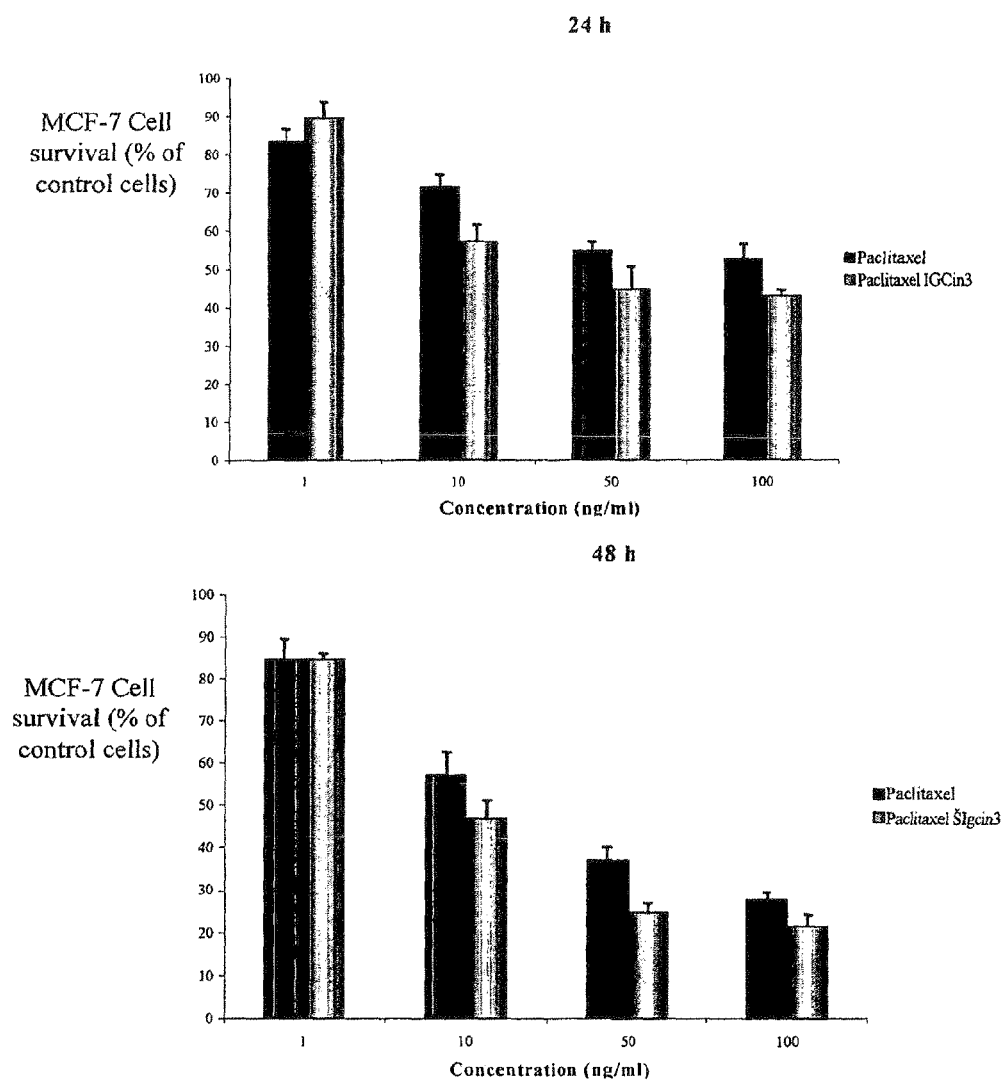

HYPERBRANCHED POLYMERS BASED ON CYCLODEXTRINS AND POLY (AMIDOAMINES) FOR THE CONTROLLED RELEASE OF INSOLUBLE DRUGS

CROSS-REFERENCE TO RELATED APPLICATION

This application is a National Stage entry of International Application No. PCT/EP2008/004624, filed Jun. 10, 2008, the disclosure of the prior application is hereby incorporated in its entirety by reference.

FIELD OF THE INVENTION

The present invention relates to controlled release systems for drugs and in particular comprises the use of hydrophilic polymers able to complex and dissolve in water vehicles highly hydrophobic drugs, in particular antitumor drugs such as taxanes (paclitaxel or docetaxel), camptothecin and derivatives thereof and etoposide, so that they can be administered also by injection. To date, these drugs are among the most potent known against certain types of cancer, but their administration involves serious problems due to their insolubility. The present invention also applies to sparingly soluble antiviral drugs, such as acyclovir and related drugs, which exhibit the same solubility limitations.

TECHNOLOGICAL BACKGROUND

The problem of the administration of taxanes (paclitaxel or docetaxel), camptothecin and derivatives thereof, etoposide and poorly water-soluble antiviral compounds (such as acyclovir), has still to be satisfactorily solved notwithstanding the many efforts described in literature. All the drugs mentioned above induce serious side effects in the patients, e.g. peripheral neuropathies, bradicardia, toxicity on mucus membranes and venous system.

By way of example, paclitaxel is at present formulated at a concentration of 2 mg/ml with the castor oil polyethoxylated derivative Cremophor EL®, containing 50% ethanol. The preparation is administered by injection. A serious hypersensitivity to paclitaxel is usually related to Cremophor EL®, used for its administration. As a consequence, the patients receive a pre-treatment either orally with Desametasone or intravenously with Diphenhydramine and Ranitidine before administration of Paclitaxel, to reduce the risk of hypersensitivity. This pre-treatment and the connected risks for the patient would not be necessary avoiding the use of Cremophor®. Moreover, the cost of paclitaxel treatment would be significantly lowered.

Many efforts to improve the administration of taxanes to patients are being described in literature, but to date none of them has apparently provided definitive improvements. Among said efforts, the following can be mentioned:
  Nanospheres of block copolymers loaded with paclitaxel, e.g. biodegradable compounds of methoxy-PEG-poly-caprolacton (S. Yeon Kim, et al. Biomaterials 22 (2001 1697-1704) or methoxy-PEG-polylactic-co-glycolic (PLGA) (Ji-Heung Kim et al. Polymers for advanced technologies, 10 649, 1999) or hydrophobized poly(L-lysine citramide imide) (M. Veil et al. Journal of Bioactive and compatible polymers, Vol. 15 No. 2, 99-114 (2000).
  Polymers conjugated with such water-soluble polymers as polyglutamic acid, polyaspartic acid or polylisine (U.S. Pat. No. 6,441,025), or prodrugs conjugated with polyethylene glycol derivatives.
  Inclusion complexes of paclitaxel with cyclodextrins. Cyclodextrins are cyclic oligosaccharides with 6-8 glycosidic units linked by an α-1-4 bond and characterized by a hydrophobic cavity in their structures, able to solubilize water-insoluble drugs. By way of example, 2-6-dimethyl-β-cyclodextrin is known as it forms inclusion compounds with paclitaxel, with solubility of 2.3 mmoles/l (about 3 g/l) (H. Hamahada et al., Journal of Bioscience and Bioengineering, 2006, 102, 369-371). The main drawback of inclusion complexes of taxanes with modified cyclodextrins is their poor solubility in aqueous media. In practice, the formation of complexes by mixing paclitaxel solutions in water-soluble solvents, e.g. alcohols, with aqueous solutions of cyclodextrin derivatives is at first apparently promising. However, the resulting clear solutions in time release again insoluble paclitaxel, which is subtracted from the complex as it crystallizes separately. Freeze-drying of the paclitaxel solution followed by redissolution of the residue in water also fails, as even in this case paclitaxel crystallizes off. This problem is solved only to some extent using cyclodextrin dimers. Furthermore, the individual cyclodextrins are mutually linked in these dimers by amino bridges, giving the molecule some toxicity.
  Cyclodextrin straight polymers in which cyclodextrin groups have random distribution along the polymeric chain. These polymers suffer, in the formation of complexes with paclitaxel or similar drugs, from the same restrictions as free cyclodextrins, as cooperation of the different cyclodextrin units present in the polymer is hindered in that they are distributed along the polymeric chain and thus distant when the polymer in solution acquires a comparatively distended conformation.

As regards camptothecin, to overcome its stability (opening of the lactone ring to the carboxylate form) and solubility problems several approaches have been investigated. In particular, the complexation with α-cyclodextrins increases the stability of captothecin, thus ameliorating the solubility and cytotoxicity profile (Kang et al. Eur. J. Pharm. Biopharm. 2002, 15, 163-170).

Acyclovir has short half-life (about 2 h) and its absorption is not complete (bioavailability about 15-30%). Due to its limited oral bioavailability Acyclovir must be taken orally five times a day (200 mg every 4 h), while intravenous formulations (5 mg/kg) must be administered every 8 hours for at least 5 days. Moreover, the intravenous dose of Acyclovir should be administered slowly over 1 hour to prevent precipitation in renal tubules.

To increase the efficacy of antiviral drugs various delivery approaches have been proposed, like encapsulation in poly (iso-butylcyanoacrylate) nanocapsules (Hillaireau er al. Int, J, Pharm. 2006, 324, 37-42. Particulate delivery systems could be able to promote sustained delivery of the antiviral drug. PLGA microparticles containing acyclovir for topical administration have been developed (de Jalon, 2001, 226, 181, 184) and acyclovir-loaded nanoparticles showed increased efficacy against herpex simplex virus type I in cell culture (de Jelon et al. Europ. J. Pharm. Biopharm. (2003) 56, 183-187). Semi-interpenetrating polymer network microspheres of acrylamide grafted on dextran or chitosan carrying up to 79% of acyclovir were prepared by emulsion-crosslinking method (Rokhade et al. Carbohydrate Polym. (2007) 605-607).

To enhance the oral bioavailability of acyclovir prodrugs have also been designed (Eur. J. Pharmac. Sci. 2004, 23, 319-325).

A poly(amidoamine) (PAA) copolymer with β-cyclodextrin can solubilise by complexation up to 11% w/w of the drug and the Acyclovir complex exhibits a higher antiviral activity than the free drug against herpes simplex virus type I in cell cultures (Bencini et al. J. Control. Release 2008, 126, 17-25).

BRIEF DESCRIPTION OF THE DRAWINGS

FIG. 1 shows a general structure of the hyperbranched PAA/cyclodextrin polymers according to the invention.

FIG. 2 shows the structure of the hyperbranched PAA/β-cyclodextrin polymer of Example 1.

FIG. 3 shows a $^1$H NMR spectrum of the hyperbranched PAA/β-cyclodextrin polymer of Example 1.

FIG. 4 shows a MALDI-TOF spectrum of the hyperbranched PAA/β-cyclodextrin polymer of Example 1.

FIG. 5 shows a schematic representation of the hyperbranched PAA/β-cyclodextrin synthesized in Example 2 with N,N'-dimethylacrylamide as a monofunctional chain terminator.

FIG. 6 shows a $^1$H NMR spectrum of the hyperbranched PAA/β-cyclodextrin polymer of Example 2.

FIG. 7 shows a TEM micrograph of the polymer of Example 3 in an aqueous dispersion.

FIG. 8 shows a Differential Scanning Calorimetric (DSC) analysis of the polymer of Example 3.

FIG. 9 shows a TEM micrograph of the paclitaxel complex of the polymer of Example 3 before (a) and after (b) lyophilization of the aqueous dispersion of the polymer.

FIG. 10 shows an in vitro release kinetics of paclitaxel from its complex with a hyperbranched PAA/cyclodextrin polymer.

FIG. 11 shows the results of in vitro cytotoxicity assays of free paclitaxel and its complex with a hyperbranched PAA/cyclodextrin polymer.

DETAILED DISCLOSURE OF THE INVENTION

The present invention relates to novel hyperbranched polymers in which cyclodextrin units are linked by ether groups to short segments of poly(amidoamines) and are prepared by Michael polyaddition of α-, β- or γ-cyclodextrins and amines to bisacrylamides. A scheme of the structure of the polymers of the invention is reported in FIG. 1.

These polymers are completely soluble in water and those which are slightly crosslinked are highly hydrophilic and give clear water suspensions which simulate solutions. In many cases, these polymer suspensions are in the form of nanoparticles.

Preferably, poly(amidoamine) segments are of amphoteric nature, e.g. the amine comonomer is 2-methylpiperazine and the bisacrylamide is 2,2-bisacrylamidoacetic acid. In fact, amphoteric poly(amidoamines), in particular the poly(amidoamine) named ISA 23, obtained from the monomers indicated above, proved highly biocompatible, as they are not recognised by the defence systems of the organism and able to circulate for a long time in healthy laboratory animals, while in tumor-bearing laboratory animals they are selectively concentrated in the tumor mass due to the so-called EPR effect ("Enhanced Permeation and Retention Effect"). This effect is due to high molecular weight polymers present in blood circulation being unable to cross the walls of normal capillaries, but able to cross the more disconnected ones of neoforming capillaries in the tumor mass. Once penetrated in the tumors they hardly exit, as tumors do not have an efficient lymphatic drainage. Moreover, these poly(amidoamines) have very high ability to dissolve water-insoluble substances, as they are highly hydrophilic. Finally, said poly(amidoamines) can be easily functionalized by introducing peptide units capable to ensure a precise direction towards target cells or cells groups, for instance tumour cells.

More particularly, the present invention relates to polymers in which:
the cyclodextrin units (CD, see FIG. 1) derive from α-cyclodextrin, β-cyclodextrin or γ-cyclodextrin or derivatives thereof in which at least one of the hydroxyls has been transformed into alkoxy groups;
the polyamidoamine segments have the structure reported below:

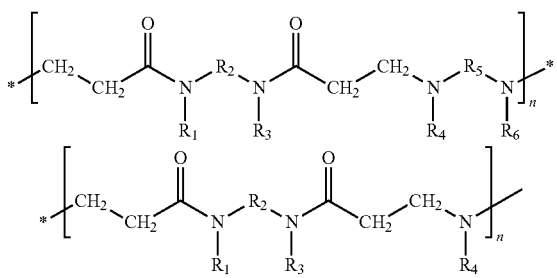

in which:
$R_1$ and $R_3$, which can be the same or different, are H or a $C_{1-4}$ alkyl group;
$R_2$ is a $C_{1-4}$ alkylene group;
or
$R_1$, $R_2$ and $R_3$ are part of a single cyclic structure, which in turn bears side substituents of the same nature as $R_1$ and $R_3$;
$R_4$ and $R_6$, which can be the same or different, are H, or a $C_{1-6}$ alkyl group, or one of said residues in turn bearing side substituents of the same nature as $R_1$ and $R_3$;
or
$R_4$, $R_5$ and $R_6$ are part of a single cyclic structure, which in turn bears side substituents of the same nature as $R_1$, $R_2$ and $R_3$;
or
$R_1$, $R_2$, $R_3$, $R_4$, $R_5$ and $R_6$ are alkyl or alkylene groups defined as above bearing in their turn additional substituents such as: primary, secondary or tertiary amino groups; carboxylic groups; sulfonic groups; phosphoric groups; alcohol hydroxy groups;
n ranges from 1 to 50, preferably from 2 to 10.

The simplified structure of said polymers is reported in FIG. 1. In the polymers, cyclodextrin units are linked through one or more hydroxyls by ether bonds to the poly(amidoamine) segments, for example as illustrated in FIG. 2.

As stated above, the polymers of the present invention are obtained by Michael polyaddition of mixtures of primary or secondary amines and alkali-activated cyclodextrins to bisacrylamides. Polymerization is carried out at temperatures ranging from 10 to 60° C., preferably from 20 to 35° C., for times ranging from 1 hour to 8 days, preferably from 8 hours to 3 days and most preferably from 1 to 2 days. The solvents used are preferably protic, most preferably water.

The polymers of the present invention can be used for solubilizing and carrying water-insoluble active molecules. Preferably, the polymers of the invention allow the preparation of aqueous injectable pharmaceutical formulations of sparingly water-soluble drugs, in particular taxanes, camptothecins and derivatives, acyclovir and related drugs. Said formulations will contain 20 mg/ml to 160 mg/ml of a polymer of the invention, preferably containing 1 mg/ml to 8 mg/ml of the active molecule in the case of docetaxel or paclitaxel, 1 mg/ml to 10 mg/ml in the case of camptothecin or analogous derivatives and 1 to 20 mg/ml in the case of acyclovir and related drugs. Furthermore, said formulations can contain other cosolvents or excipients conventionally used and fulfilling the regulatory requirements for the preparation of injectable formulations.

The polymers of the invention and the formulations thereof can be freeze-dried. The resulting solid products can be easily resuspended in water upon simple hand stirring, both in the presence and in the absence of any active molecules.

The hyperbranched, non-crosslinked (or with a controlled crosslinking degree) structure, is obtained suitably varying the stoichiometry of the starting mixture, the temperature and the reaction time.

The preparation procedure employed is based on the following theoretical premise.

The polymerization reaction involved is a stepwise polyaddition. It is well known that in polymerizations involving monomers carrying separately two complementary functions "a" and "b", where "a" is by convention the minority function, the two parameters ruling the process are the initial stoichiometric ratio "r", defined as $$r = \frac{Na_o}{Nb_o} \quad (1)$$

where $Na_o$ and $Nb_o$ are the number of a and b functions initially present and conversion degree "p", defined as:

$$p = \frac{Na_o - Na}{Na_o} \quad (2)$$

where Na is the number of a functions present at the observation time.

By definition, both r and p are obviously $\leq 1$.

Stepwise polymerizations involving monomers bearing more than two functional groups (multi- or polyfunctional stepwise polymerizations) may lead to insoluble crosslinked products at p values higher than a particular value "$p_c$", called "critical advancement degree". For $p > p_c$ the system looses its mobility, and for this reason $p_c$ is also called "gel point".

When the functions related to the polyfunctional monomers are of only one type, the critical advancement degree $p_c$, is represented by the Flory-Stockmayer equation (see for instance: G. Odian "Principles of Polymerization" 3rd Ed, John Wiley & Sons, USA, 1991):

$$p_c = \frac{1}{\{r[1 + \rho(f-2)]\}^{1/2}} \quad (3)$$

Where $\rho$ is the fraction of functions belonging to the monomer with functionality >2 with respect to the total amount of the functions of the same type initially present in the system:

$$\rho = \frac{a^f}{a_0} \quad (4)$$

and r is defined as above.

It is evident that in Eq. (3) $p_c$ and r are related. In particular, it exists a critical stoichiometric ratio, that we sign $r_c$ under which the system is unable to gel and yields hyperbranched but still soluble polymers.

Since p (and therefore also $p_c$) cannot be >1, the theoretical $r_c$ value is obtained from Eq. (3) by assuming $p_c = 1$ and solving for r. Then we have:

$$r_c = \frac{1}{1 + \rho(f-2)} \quad (5)$$

and, if $\rho = 1$, that is, in the system the polyfunctional monomer is the only one bearing that kind of function, Eq. (4) will be reduced to:

$$r_c = \frac{1}{f-1} \quad (6)$$

Eq. 5 provides a convenient tool for determining the active functions of a potentially multifunctional monomer, that is, in the present case, the number of hydrogens of the multifunctional monomer, that is, cyclodextrins, amenable to addition reaction. This can be achieved by experimentally determining the $r_c$ value for stoichiometrically imbalanced reactant mixtures with excess double bonds. Operationally, a series of imbalanced reaction mixtures with progressively larger excess double bonds will be allowed to polymerize for a time sufficient to reach the maximum conversion degree. The minimum double bonds excess inhibiting gelation immediately leads to $r_c$ and then to $f$. Under the reaction conditions adopted, $f$ of β-cyclodextrin was determined and found in the range 5.5-6.

Moreover, both Eqs (3) and (5) can be utilized for obtaining soluble hyperbranched polymers or crosslinked polymers with a controlled crosslinking degree. In fact, by $r < r_c$ at all conversion degrees hyperbranched, but not crosslinked products will be obtained. Conversely, by $r > r_c$, hyperbranched, but not crosslinked products will be obtained by conversion degree $p < P_c$ and crosslinked products by conversion degrees $p > p_c$.

In both cases, slightly crosslinked products will be obtained by $r \geq r_c$, or $p \geq p_c$, that is, when both values differ only slightly from the critical values.

It is commonly acknowledged that Eq. (3) is not valid in the presence of monofunctional compounds; for these systems the following alternative equation has been elaborated:

$$p_c = \frac{1}{[r(f_{W,A} - 1)(f_{W,B} - 1)]^{1/2}} \quad (6)$$

where $f_{W,A}$ and $f_{W,B}$ are the weight average of the monomers functionalities (including the monofunctional ones), defined as:

$$f_{W,A} = \frac{\sum f_{A,j}^2 N_{A,j}}{\sum f_{A,j} N_{A,j}}; \quad (7)$$

$$f_{W,B} = \frac{\sum f_{B,j}^2 N_{B,j}}{\sum f_{B,j} N_{B,j}} \quad (8)$$

in which "$f_{A,j}$" and "$f_{B,j}$" represent the functionality of each monomer of type "A" and "B" respectively and where "$N_{A,j}$" and "$N_{B,j}$" are the corresponding moles number in the system (see for instance G. Odian "Principles of Polymerization" 3rd Ed, John Wiley & Sons, USA, 1991).

Also in this case it's possible to define a critical ratio, $r_c$, under which the system is unable to gel and yields hyperbranched but still soluble polymers. This will be determined putting $p_c=1$ and solving for r. The resultant equation is $$r_c = \frac{1}{(f_{w,A}-1)(f_{w,B}-1)} \quad (9)$$

What stated above will be further illustrated by the following examples.

Example 1

In a two-necked round-bottom flask equipped with magnetic stirrer and nitrogen inlet, 2,2-bis(acrylamido)acetic acid BAC (8 mmol, 1.6147 g; 98.18%) and lithium hydroxide monohydrate (8 mmol, 0.3990 g; 99.00%) were dissolved in distilled water (4.5 ml) under nitrogen flow. 2-Methyl piperazine MeP, purified before by crystallization, was added (4 mmol, 0.4282 g; 93.56%). After complete dissolution, β-cyclodextrin (1 mmol, 1.1464 g; 0.99%, containing 13.7% w/w of water) and lithium hydroxide monohydrate (4.5 mmol, 0.1907 g; 99.00%) were added. The pH of the reaction mixture was 12.5. The reaction was maintained for 24 hours at 28° C., in the dark, under nitrogen atmosphere. The solution was then diluted with distilled water (20 ml), acidified to pH 3 with HCl 37%, ultrafiltered through a membrane with nominal molecular weight cut off 3000 and finally lyophilized. The yield was 72%.

$^1$H NMR analysis of the product indicated a β-cyclodextrin content 39.5% (w/w) (FIG. 3). LS-SEC online analysis indicated a $\overline{M}_n$ of 7000 and a $\overline{M}_w$ of 17000.

MALDI TOF analysis is shown in FIG. 4. It is consistent with a distribution of macromolecules bearing β-cyclodextrin units connected by BAC/MeP segments.

Example 2

In a two-necked round-bottom flask equipped with magnetic stirrer and nitrogen inlet, 2,2-bis(acrylamido)acetic acid BAC (8 mmol, 1.6147 g; 98.18%) and lithium hydroxide monohydrate (8 mmol, 0.3990 g; 99.00%) were dissolved in distilled water (3 ml) under nitrogen flow. 2-Methyl piperazine MeP, purified before by crystallization, was added (4 mmol, 0.4282 g; 93.56%). After complete dissolution, β-cyclodextrin (1 mmol, 1.1464 g; 0.99%, containing 13.7% w/w of water), lithium hydroxide monohydrate (4.5 mmol, 0.1907 g; 99.00%) and, finally, N,N-dimethylacrylamide (6.891 mmol, 0.697 g; 99.13%) were added. The pH value of the reaction mixture was 12.5. The reaction mixture was allowed to react for a week at 30° C., in the dark, under nitrogen flow. The product was then isolated and purified as in the previous case. The yield was 63.8%. The structure of this polymer is reported in FIG. 5.

$^1$H NMR analysis of the product is reported in FIG. 6. It gives evidence of a β-cyclodextrin content of 39.36% (w/w). LS-SEC online indicated a $\overline{M}_n$ of 8700 and a $\overline{M}_w$ of 36300.

Example 3

The reaction was carried out as reported in Example 1, by using 3.0 ml water instead of 4.5 ml. In these conditions a slightly crosslinked but highly hydrophilic product was obtained, that in water gave rise to fine and clear dispersions simulating solutions. These were analyzed by TEM microscopy, whose results, shown in FIG. 7, clearly demonstrate the nanosized particle dimensions.

Example 4

The reaction was carried out as reported in Example 1, by substituting α-cyclodextrin (0.973 g) for β-cyclodextrin. The resultant polymer had a cyclodextrin content of 33% by weight ($^1$H NMR data). LS-SEC online indicated a $\overline{M}_n$ of 14000 and a $\overline{M}_w$ of 38000. Yield=59%.

Example 5

The reaction was carried out as reported in Example 1, by substituting γ-cyclodextrin (1.297 g) for β-cyclodextrin. The resultant polymer had a cyclodextrin content of 40% by weight ($^1$H NMR data). LS-SEC online indicated a $\overline{M}_n$ of 17000 and a $\overline{M}_w$ of 42000. Yield=67%.

Example 6

The reaction was carried out as reported in Example 1, by substituting NN'-dimethylethylenediamine (0.353, 4 mmol) for 2-methylpiperazine. The resultant polymer had a cyclodextrin content of 44% by weight ($^1$H NMR data). LS-SEC online indicated a $\overline{M}_n$ of 16000 and a $\overline{M}_w$ of 48000. Yield=66%.

Example 7

This example reports the experimental determination of the number of functions of β-cyclodextrin ($f_{exp}$) and the preparation of a series of hyperbranched polymers either crosslinked or entirely soluble.

The β-cyclodextrin molecule contains seven primary hydroxyl groups, and is therefore able, in principle, to undergo Michael addition with seven activated double bonds. In other words, β-cyclodextrin could be considered as a heptavalent monomer. However, under the conditions adopted, the actual functionality may be lower mainly owing to steric hindrance, which increases as the reaction proceeds. Therefore, in order to control the reaction, the actual functionality $f$ was experimentally determined by performing a set of reactions in which the molar ratio between the reacting species (r) was equal to the critical molar ratio ($r_c$) calculated by hypothesizing different β-cyclodextrin functionalities in the range 4.5-6.0, allowing the reaction to go near completion, and observing the occurrence of gelation, if any. All the reactions were carried out at temperature of 28° C. The results are shown in Table 1.

The results of Table 1 clearly indicate that, under the conditions adopted, the actual $f$ of β-cyclodextrin lies in between 5.5 and 6.

TABLE 1

Determination of β-cyclodextrin's functionality f in Michael type addition to bisacrylamides under the condition adopted, by experimentally determining the critical monomers ratio $r_c$.

| Code | BAC (mmol) | MeP (mmol) | βCD (mmol) | Hypothetic f | r | $r_c$* | The state of the product |
|---|---|---|---|---|---|---|---|
| 1 | 12.25 | 4 | 1 | 4.5 | 0.5263 | 0.5263 | Crosslinked |
| 2 | 14.00 | 4 | 1 | 5.0 | 0.4642 | 0.4642 | Crosslinked |
| 3 | 16.37 | 4 | 1 | 5.5 | 0.4122 | 0.4122 | Crosslinked |
| 4 | 19.00 | 4 | 1 | 6.0 | 0.3684 | 0.3684 | Soluble hyper-branched |

*Calculated according to the hypothesized f (see previous column).

Example 8

This example reports on the solubilizing ability of the hyperbranched PAA-cyclodextrin polymers.

The solubilization capacity of polymers was determined using paclitaxel as model of very poor-water soluble drug. 4 mg of paclitaxel were added to screw-capped vials containing 3 ml of each type of polymer aqueous solutions at a concentration of 23 mg/ml. The mixtures were incubated under stirring for 24 h. All the polymers were able to solubilize paclitaxel forming an opalescent nanosuspension. All samples were centrifuged and the supernatants were analysed by reverse-phase HPLC using a C18 column and detected at 227 nm. The mobile phase was ammonium acetate 0.17 M pH 5.0:methanol:acetonitrile (50:10:40 v/v)) mixture. The polymers significantly enhanced the aqueous solubility of paclitaxel. The concentration of paclitaxel in the supernatants ranged from 1.25 mg/ml to 3.8 mg/ml according to the structure of the polymer.

Example 9

This example reports on the paclitaxel loading capacity of the soluble and slightly crosslinked hyperbranched PAA-cyclodextrin polymers.

The paclitaxel loading capacity was determined using freeze-dried samples. About 5 mg of paclitaxel polymer freeze-dried solid were weighed and dissolved in methanol. After dilution with the mobile phase the amount of drug was determined by reverse-phase HPLC using a C18 column and detected at 227 nm. The mobile phase was ammonium acetate 0.17 M pH 5.0:methanol:acetonitrile (50:10:40 v/v)) mixture. The percentages of paclitaxel-loaded are reported in Table 2.

TABLE 2

Paclitaxel loading capacity of soluble and slightly crosslinked hyperbranched PAA-cyclodextrin polymers.

| Polymer | Percentage of drug loaded (w/w) |
|---|---|
| Product of Example 3 | 4.63 |
| Product of Example 2 | 3.20 |
| Product of Example 1 | 1.17 |
| Product of Example 6 | 2.15 |

Example 10

This example reports on the determination of thermal stability of the hyperbranched PAA-cyclodextrin polymers.

Differential Scanning Calorimetry (DSC) analysis was used to determine the thermal stability of the series of polymers. About 3 mg of polymer were weighed in aluminum sample pans and then heated at a rate of 10° C./min in the 25-300° C. range under a nitrogen purge using a DSC 7 calorimeter (Perkin Elmer). A typical tracing is reported in FIG. 8. All polymers were stable up to at least 200° C. This could allow the sterilization in autoclave.

Example 11

This example reports on the stability of the hyperbranched PAA-cyclodextrin polymers/paclitaxel complexes towards freeze-drying of their aqueous nanosuspensions.

The paclitaxel nanosuspensions of the different polymers were freeze dried obtaining a dried powder which could easily resuspended in water by shaking without aggregation phenomena.

Transmission Electron Microscopy of drug nanosuspensions before and after freeze-drying was carried out to verify the morphological aspect of the samples. The photomicrograph of slightly crosslinked polymer carrying paclitaxel before and after freeze-drying are reported in FIG. 9 showing that the system maintained its structure and the drug did not crystallize.

Example 12

This example reports on the determination of in vitro release kinetics of paclitaxel from its complexes with hyperbranched PAA-cyclodextrin polymers.

The in vitro release of paclitaxel from the polymeric systems were conducted using a dialysis membrane bag (cut off 3000 Da) and 1% SDS solution as a sink medium. The whole bag was placed in 50 ml of the SDS solution. At fixed time 0.5 mL of the solution were withdrawn and the paclitaxel concentration analysed by the HPLC method.

Typical release curves are reported in FIG. 10.

Example 13

This example reports on the determination of the in vitro cytotoxicity assay of paclitaxel complexes with hyperbranched PAA-cyclodextrin polymers.

Human breast carcinoma cells (MCF-7) were grown in monolayer in RPMI 1640 medium supplemented with 10% heat-inactivated foetal bovine serum and antibiotics at 37° C. in a humidified atmosphere containing 5% $CO_2$. Exponentially growing cells were seeded in 24-well plates and treated for 24 and 48 h with various concentration of paclitaxel (free or carried in the slightly crosslinked polymer)). The concentrations of paclitaxel varied from 0.5 to 3.0 µg/ml for solution and nanosponges.

Cell viability was assessed by trypan blue dye exclusion assay. Cytotoxicity was expressed as percentage of control cells (untreated cells). Cytotoxicity studies of paclitaxel reveled that the complex is more potent than the plain paclitaxel as shown by the graphs reported in FIG. 11.

Example 14

This example reports on the determination of the camptothecin loading capacity of hyperbranched PAA-cyclodextrin polymers. The results are shown in Table 3.

TABLE 3

Campothecin loading capacity of hyperbranched PAA-cyclodextrin polymers.

| Polymer | w/w Percent of camptothecin in the complex |
|---|---|
| Product of Example 1 | 0.25 |
| Product of Example 2 | 0.92 |
| Product of Example 3 | 12.94 |

The invention claimed is:

1. Hyperbranched, water-soluble polymers, obtained by Michael polyaddition of α-, β-, or γ-cyclodextrins and amines to bisacrylamides, wherein the polymers comprise polyamido-amino segments.

2. The polymers as claimed in claim 1 wherein at least one of the hydroxyl groups of α-cyclodextrin, β-cyclodextrin or γ-cyclodextrin or derivatives thereof has been transformed into methoxy groups.

3. The polymers as claimed in claim 1, wherein the polyamido-amino segments have the following formula

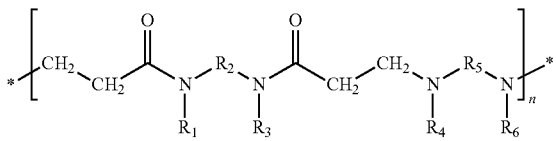

-continued

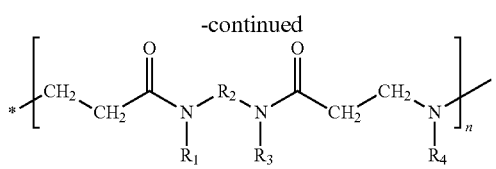

in which:
$R_1$ and $R_3$, which can be the same or different, are H or a $C_{1-4}$ alkyl group;
$R_2$ and $R_5$ are a $C_{1-4}$ alkylene group;
or
$R_1$, $R_2$ and $R_3$ are part of a single cyclic structure comprising side substituents, wherein the side substituents are H or $C_{1-4}$ alkyl groups;
$R_4$ and $R_6$, which can be the same or different, are H, or a $C_{1-6}$ alkyl group, or one of the same residues comprising side substituents, wherein the side substituents are H or $C_{1-4}$ alkyl groups;
or
$R_4$, $R_5$ and $R_6$ are part of a single cyclic structure comprising side substituents, wherein the side substituents are H or $C_{1-4}$ alkylene groups or $C_{1-4}$ alkyl groups;
or
$R_1$, $R_2$, $R_3$, $R_4$, $R_5$ and $R_6$ are alkyl or alkylene groups as defined above and further comprise substituents selected from primary, secondary or tertiary amino groups; carboxylic groups; sulfonic groups; phosphoric groups; hydroxy alcohol groups;
n ranges from 1 to 50.

4. Pharmaceutical formulations comprising a polymer as claimed in claim 1, a water-insoluble drug, and pharmaceutically acceptable excipients, wherein the polymer is present in an amount sufficient to solubilize the water-insoluble drug.

5. The pharmaceutical formulations as claimed in claim 4, wherein the water-insoluble drugs are selected from taxanes, camptothecin and derivatives thereof, etoposide and acyclovir.

* * * * *